United States Patent
Chang et al.

(10) Patent No.: US 9,539,285 B2
(45) Date of Patent: Jan. 10, 2017

(54) COMPOSITION FOR TREATING INTRAVENTRICULAR HEMORRHAGE IN PRETERM INFANTS COMPRISING MESENCHYMAL STEM CELLS

(71) Applicant: SAMSUNG LIFE PUBLIC WELFARE FOUNDATION, Seoul (KR)

(72) Inventors: Yun Sil Chang, Seoul (KR); Won Soon Park, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 219 days.

(21) Appl. No.: 13/655,356

(22) Filed: Oct. 18, 2012

(65) Prior Publication Data

US 2014/0072527 A1 Mar. 13, 2014

(30) Foreign Application Priority Data

Sep. 7, 2012 (KR) .......................... 10-2012-0099413

(51) Int. Cl.
| | | |
|---|---|---|
| A61K 35/26 | (2015.01) | |
| A61K 35/28 | (2015.01) | |
| A61K 38/18 | (2006.01) | |
| A61K 38/20 | (2006.01) | |
| A61K 38/28 | (2006.01) | |
| A61K 9/00 | (2006.01) | |

(52) U.S. Cl.
CPC ............. *A61K 35/28* (2013.01); *A61K 9/0019* (2013.01); *A61K 38/18* (2013.01); *A61K 38/2066* (2013.01); *A61K 38/28* (2013.01)

(58) Field of Classification Search
None
See application file for complete search history.

(56) References Cited

U.S. PATENT DOCUMENTS

| | | | |
|---|---|---|---|
| 2009/0232782 A1* | 9/2009 | Fu ................................ | 424/93.7 |
| 2010/0226896 A1* | 9/2010 | Dracker ....................... | 424/93.7 |
| 2013/0259845 A1 | 10/2013 | Heidaran et al. | |

FOREIGN PATENT DOCUMENTS

| | | | |
|---|---|---|---|
| EP | 2 298 328 B1 | 4/2014 | |
| KR | 10-2010-0100855 A | 9/2010 | |
| WO | WO 2007124594 | * 11/2007 | |

OTHER PUBLICATIONS

Experimental Neurology, 2005, v.193, pp. 249-250.*
Hudgins et al., Pediatr. Neurosurg. 1997, v.26, pp. 281-287.*
Office Action dated Nov. 29, 2013 of the corresponding Korean Patent Application No. 2012-0099413—5 pages.
Notice of Allowance dated May 29, 2014 of corresponding Korean Patent Application No. 2012-0099413—2 pages.
Andrews et al., "Fibrinolytic therapy in intraventricular hemorrhage," *The Annals of Pharmacotherapy*, vol. 35(11), pp. 1435-1448 (Nov. 2001).
Coplin et al., "A Cohort Study of the Safety and Feasibility of Intraventricular Urokinase for Nonaneurysmal Spontaneous Intraventricular Hemorrhage," *Stroke*, vol. 29, pp. 1573-1579 (Aug. 1998).
Popa et al., "Acetazolamide therapy evaluation in haemorrhagic stroke," *Rom J Neurol Psychiatry*, vol. 33(2), pp. 145-155 (Apr. 1995).
Whitelaw et al., "Diuretic therapy for newborn infants with posthemorrhagic ventricular dilatation," *The Cochrane Library*, Issue 2, pp. 1-21, Wiley (2001).
Whitelaw et al., "Intraventricular streptokinase after intraventricular hemorrhage in newborn infants," *The Cochrane Library*, Issue 4, pp. 1-11 (2007).
Ahn et al., "Human MSC transplantation attenuates post hermorrhagic hydrocephalus in the newborn rat model of severe intraventricular hemorrhage", Ogram and Abstracts, The 61st annual fall meeting of the Korean Pediatric Society, Seoul, Korea, Oct. 21, 2011.
Ahn, et al., Human Umbilical Cord Blood Derived Mesenchymal Stem Cells Transplantation Attenuates Post Hemorrhagic Ventricular Dilatation after Severe Intraventricular Hemorrahage in the Newborn Rats (Abstract #: 755102) ASPR poster, Pediatric Academic Societies' Annual Meeting in Boston, Massachusetts, Apr. 28, 2012.

* cited by examiner

*Primary Examiner* — Michail Belyavskyi
(74) *Attorney, Agent, or Firm* — Harness, Dickey & Pierce, P.L.C.

(57) ABSTRACT

Disclosed is a composition for the prophylaxis or therapy of intraventricular hemorrhage in preterm infants comprising mensenchymal stem cells. Functioning to prevent ventricular dilatation and reduce the level of inflammatory cytokines in cerebrospinal fluid, the composition comprising mesenchymal stem cells is advantageously useful for the prophylaxis or therapy of intraventricular hemorrhage in preterm infants. Accordingly, the composition is effectively preventive of hydrocephalus which occurs subsequent to intraventricular hemorrhage. In addition, the composition makes not only a histological and biochemical recuperation in the intraventricular hemorrhage-injured brain, but also significantly improves sensory motor functions. Mesenchymal stem cells can be used as an effective therapeutic agent because they are less prone to induce immune rejection responses and are highly likely to secrete proliferative, differentiative, and regulatory factors. Hence, mesenchymal stem cells are expected to play a critical role in the therapy of intraventricular hemorrhage in preterm infants.

8 Claims, 7 Drawing Sheets

COMPOSITION FOR TREATING INTRAVENTRICULAR HEMORRHAGE IN PRETERM INFANTS COMPRISING MESENCHYMAL STEM CELLS

A. BACKGROUND OF THE INVENTION

1. Field of the Invention

The present invention relates to a composition for the prophylaxis or therapy of intraventricular hemorrhage and hydrocephalus in preterm infants, comprising mesenchymal stem cells.

2. Description of the Related Art

According to the WHO, preterm infants are babies born before completing 37 weeks gestation or before 259 days from the first day of the last menstrual period. Regardless of gestational age, low birth weight (LBW) is defined as a birth weight of a liveborn infant of less than 2,500 g, very low birth weight (VLBW) as a birth weight of a liveborn infant of less than 1,500 g, and extremely low birth weight (ELBW) as a birth weight of a liveborn infant of less than 1,000 g. Underdeveloped lungs make it difficult for preterm infants to breathe by themselves. In many cases, preterm infants further suffer from various diseases due to many other premature organs. The most representative among neurological diseases of preterm infants which leave complications for a long period of time or for their lives is intraventricular hemorrhage. Once intraventricular hemorrhage occurs, blood flows to the brain's ventricular system. Intraventricular hemorrhage in preterm infants is often described in the following four grades:

Grade 1—bleeding occurs just in the germinal matrix below and adjacent to the ventricles.

Grade 2—bleeding also occurs inside the ventricles.

Grade 3—ventricles are enlarged by the blood.

Grade 4—there is bleeding into the brain tissues around the ventricles.

Grades 1 and 2 are most common in preterm infants, and often there are no further complications because blood left after slight hemorrhage is for the most part absorbed and spontaneously healed. Grades 3 and 4 are the most serious and may result in long-term brain injury to the infant, with the accompaniment of complications including, for example, hydrocephalus (an abnormal accumulation of cerebrospinal fluid in the ventricles), convulsion, and cerebral palsy. With cerebral palsy, patients exhibit physical disability in development, chiefly in various areas of body movement, notably in the limbs, for a long period of time and often for their lives.

Intraventricular hemorrhage in preterm infants is quite different from the intracranial hemorrhage frequently observed in adults in terms of cause, bleeding locus, pathological physiology, and therapeutic modality. No certain therapy has yet been established for intraventricular hemorrhage in preterm infants, which is one of the greatest barriers to preventing or treating neonatal complications. In adults, primary spontaneous cerebral hemorrhage is, for the most part, intracerebral hemorrhage which occurs due to a spontaneous rupture of cerebral vessels. By contrast, almost all cases of cerebral hemorrhage in preterm infants are accounted by the intraventricular hemorrhage which occurs when small vessels around the germinal matrix burst and bleed into adjacent ventricles. Turning to anatomic correlations, there is a difference in the primary outbreak site of cerebral hemorrhage between adults and preterm infants. In adults, the most frequent location in terms of the occurrence of cerebral hemorrhage is at the level of the basal ganglia which are supplied by the cerebral artery bifurcations, whereas the germinal matrix, a highly vascularized, fragile region of the brain, is the most frequent location. Also, the difference of intracerebral hemorrhage between adults and preterm infants is found at mechanisms and pathophysiology. The anatomical and physiological prematurity of organs in preterm infants does not ensure constant blood pressure for the brain, so that cerebral vessels are greatly modulated in pressure. Preterm infants are also more prone to developing hyperglycemia or suffer from a rapid change in blood electrolyte level because of their decreased ability to regulate their blood sugar and electrolytes. In addition to these, other problems with physiological prematurity, such as insufficient regulatory ability in response to a body temperature change, a change in body's acidity with respiratory and metabolic conditions, etc., may induce intracerebral hemorrhage. In contrast, most causes of adult intracerebral hemorrhage are caused by tumors, traumas, and vascular diseases such as hypertension, diabetes, etc. Thus, differences between adults and preterm infants not only in the cause and type of intracerebral hemorrhage, but also in their anatomy and pathophysiology, require different therapies. In recent years, extensive studies have been done on the use of stem cells in therapy for cerebral infarction and hemorrhage. However, the application of stem cells to the therapy of intracerebral hemorrhage in preterm infants has not been previously reported, despite the high incidence.

There are reports that, of various kinds of stem cells, mesenchymal stem cells do not elicit alloreactive lymphocyte proliferative responses and that infusion or implantation of allogeneic, major-histocompatibility-mismatched mesenchymal stem cells into baboons has been well tolerated. The low immunogenic nature of mesenchymal stem cells is attributed to the fact that their cytokines and other secretions act to suppress immune responses of surrounding environments.

Given the background, the present inventors made a rational deduction that the use of mesenchymal stem cells, not autogenic, but allogeneic, in the prophylaxis and therapy of intraventricular hemorrhage and its hydrocephalus complications in preterm infants is ideal and most reasonable, and proved the deduction true in animal tests for the first time, which led to the present invention.

B. SUMMARY OF THE INVENTION

Accordingly, the present invention has been made keeping in mind the above problems occurring in the prior art, and an object of the present invention is to provide a composition for the prophylaxis or therapy of intraventricular hemorrhage and subsequently occurring hydrocephalus in preterm infants, comprising mesenchymal stem cells, which are easy to use and advantageous in transplantation, as an active ingredient.

In accordance with an aspect thereof, the present invention addresses a composition for the prophylaxis or therapy of intraventricular hemorrhage in preterm infants, comprising mesenchymal stem cells as an active ingredient. Also contemplated in accordance, with another aspect of the present invention is a method for preventing or treating intraventricular hemorrhage in preterm infants, comprising administering mesenchymal stem cells.

After serious intraventricular hemorrhage, blood clots may form or subsequent inflammation may be caused by blood clots in the arachnoid membrane which can block the flow of cerebrospinal fluid, leading to increased fluid in the brain (hydrocephalus). Thus, in one embodiment of the present invention, the intraventricular hemorrhage in preterm infants may cause subsequent hydrocephalus.

The greatest therapeutic effects of mesenchymal stem cells of various kinds of stem cells have been repeatedly observed in previous studies of the present inventors. After hyperoxia-induced pulmonary injury in immunologically healthy neonatal rats, the administration of human mesenchymal stem cells into the airways did not elicit abnormal histopathological responses in the lung of the rats. Further, nowhere have histopathological abnormalities been found in any organ including the lung of fully grown rats. In adult mouse models where acute pulmonary injury had been induced by intratracheal administration of E. coli, the intratracheal or intravenous injection of mesenchymal stem cells was found to significantly reduce pulmonary interstitial edema, pulmonary parenchymal inflammation, and parenchymal hemorrhage, compared to the non-treated control. In spite of heterotransplantation, as demonstrated in those examples, mesenchymal stem cells do not induce immune rejection thanks to their immunosuppressive nature.

In one embodiment of the present invention, the mesenchymal stem cells are used as an autograft or an allograft.

Conventional studies are concerned with the treatment of intraventricular hemorrhage by autotransplantation of stem cells. However, the present invention is achieved with allogeneic, but not autogeneic, mesenchymal stem cells. Under the practical situation that most cases of the intraventricular hemorrhage occur in extremely premature infants, it is almost impossible to take a tissue sample, such as bone marrow, skin, or adipose tissue, for use as a source of mesenchymal stem cells, from extremely premature infants who do not weigh 1,000 grams. The most possible is the isolation of mesenchymal stem cells from umbilical cord blood. In addition, the quantity of the umbilical cord blood obtainable from preterm infants whose body weight is less than even 1000 grams is very small, and because both the fetus and the mother in a perinatal period are, for the most part, hemodynamically unstable, umbilical cord blood is practically impossible to take from them. Even if umbilical cord blood is obtained, its amount is small and thus only a trace amount of mesenchymal stem cells can be obtained from the umbilical cord blood. The most important factors to the efficiency of cell therapy include dose and time. In one experiment, mesenchymal stem cells were administered at a dose of $10^7$ cells/kg of body weight 24 hours after the outbreak of intraventricular hemorrhage. When account is taken of the fact that intraventricular hemorrhage in preterm infants takes place within three days after birth, it is impossible to culture mesenchymal stem cells isolated from umbilical cord blood to the degree sufficient to bring about a significant effect in the cell therapy within a few days.

In another embodiment of the present invention, the mesenchymal stem cells may be selected from the group consisting of mesenchymal stem cells derived from umbilical cord blood, adipose tissue, skin, or bone marrow, mesenchymal stem cells proliferated from them by passage, and combinations thereof.

In another embodiment of the present invention, the composition may further comprise an auxiliary component selected from the group consisting of, but not limited to, a culture medium, an anti-inflammatory cytokine gene, an inflammatory cytokine siRNA or anti-sense primer, an expression vector carrying the siRNA or the primer, interleukin-10, a growth factor, and a combination thereof.

In a further embodiment of the present invention, the composition may be intraventricularly or intravascularly injected into the patient, but the present invention is not limited by the administration method.

Further, the composition of the present invention functions to recuperate corpus callosum thinning attributed to ventricular dilatation, prevent cell death, and reduce gliosis. In addition, the composition increases neural myelination and reduces the level of inflammatory cytokines in cerebrospinal fluid.

In accordance with a further aspect thereof, the present invention provides a formulation for the treatment of intracerebral hemorrhage, prepared from the composition. limitations are imposed on the kind of the formulation. Preferably, the formulation may be an injection or an infusion.

Functioning to prevent ventricular dilatation and reduce the level of inflammatory cytokines in cerebrospinal fluid, the composition comprising mesenchymal stem cells in accordance with the present invention is advantageously useful for the prophylaxis or therapy of intraventricular hemorrhage in preterm infants. Accordingly, the composition is effectively preventive of hydrocephalus which occurs subsequent to intraventricular hemorrhage. In addition, the composition for the prophylaxis or therapy of intraventricular hemorrhage in preterm infants makes not only a histological and biochemical recuperation in the intraventricular hemorrhage-injured brain, but also significantly improves sensory motor functions. Mesenchymal stem cells can be used as an effective therapeutic agent because they are less prone to induce immune rejection responses and are highly likely to secrete proliferative, differentiative, and regulatory factors. Hence, mesenchymal stem cells are expected to play a critical role in the therapy of intraventricular hemorrhage in preterm infants.

BRIEF DESCRIPTION OF THE DRAWINGS

The above and other objects, features and other advantages of the present invention will be more clearly understood from the following detailed description taken in conjunction with the accompanying drawings, in which.

C. DESCRIPTION OF THE PREFERRED EMBODIMENTS

Figure 1:
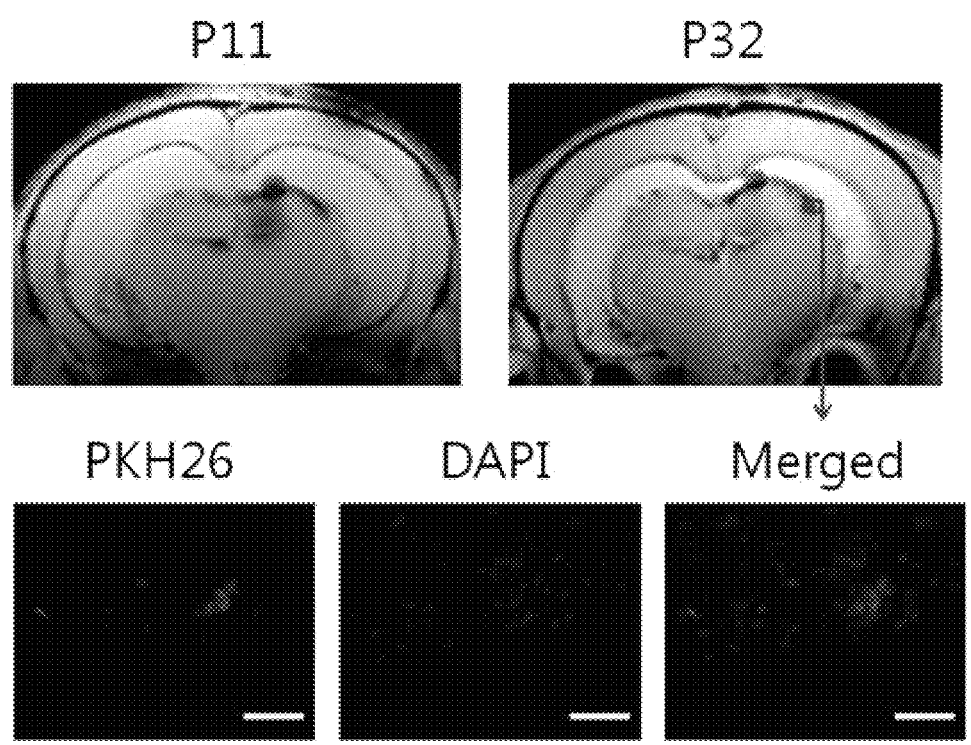
FIG. 1 shows flash MRI images and fluorescence microphotographs of the brain of an intraventricular hemorrhage-induced rat illustrating the stable settlement of a cellular therapeutic in brain tissue.

For use as an active ingredient for the therapy of intraventricular hemorrhage in preterm infants, mesenchymal stem cells are isolated from the umbilical cord blood of the human body and proliferated. The cultured mesenchymal stem cells express on their surface CD105 (99.6%) and CD73 (96.3%) while lacking the expression of CD34 (0.1%), CD45 (0.2%), and CD14 (0.1%). In addition, mesenchymal stem cells are positive to HLA-AB, but negative to HLA-DR, and express Oct4 and SSEA-4. The cells are identified to undergo osteogenic, chondrogenic, and adipogenic differentiation in vitro. This potency was retained until the $10^{th}$ passage.

Umbilical cord blood is typically collected as follows. In the case of normal delivery, blood can be harvested from the vein of the expelled umbilical cord while the placenta remains within the uterus after the birth of the baby. Upon cesarean delivery, blood is taken from the expelled umbilical cord vein, together with the placenta, from the uterus after the birth of the baby. The collection of blood from the vein of the umbilical cord which communicates the placenta with the fetus and is expelled from the uterus after delivery may be achieved using aseptic manipulation. In this regard, umbilical cord blood may be taken after delivery and before placenta separation, or ex vivo after placenta separation. In the case of cesarean delivery, umbilical cord blood is harvested ex vivo after placenta separation. A needle is inserted into a vein in the umbilical cord to drain the blood into an anticoagulant-coated blood bag.

With regard to methods of the separation and culture of mesenchymal stem cells from harvested umbilical cord blood, reference may be made to Korean Patent Laid-Open Publication No. 2003-0069115 or the literature (Pittinger M F et al., Science, 284: 143-7, 1999; and Lazarus H M et al., Bone Marrow Transplant, 16: 557-64, 1995). To quote an example, first, mononuclear cells including hematopoietic cells and mesenchymal stem cells are isolated from harvested umbilical cord blood by Ficoll-Hypaque gradient centrifugation, and washed many times to remove impurities therefrom. Then, the mononuclear cells are seeded at a suitable density into culture dishes and cultured so that they proliferate in a single layer. Of them, mesenchymal stem cells have homogenous, spindle shaped morphology and proliferate in a colony form as visualized by phase contrast microscopy. When the cells grow to confluency, they are allowed to undergo passages to proliferate to a desired number.

A medium containing 10%~to 30% FBS may be used for isolating and culturing mesenchymal stem cells. So long as it is accepted in the art, any medium may be employed to maintain mesenchymal stem cells. Examples of the medium include Dulbecco's modified eagle medium (DMEM), minimal essential medium (MEM), alpha-minimal essential medium (α-MEM), McCoy's 5A medium, Eagle's basal medium, Connaught Medical Research Laboratory (CMRL) medium, Glasgow minimal essential medium, Ham's F-12 medium, Iscove's modified Dulbecco's medium (IMDM), Liebovitz's L-15 medium, and Roswell Park Memorial Institute (RPMI) 1640 medium, with preference for DMEM. For culture, the cells are suspended at a density of approximately $5 \times 10^3 \sim 2 \times 10^4$ cells/mL in the medium.

In the present invention, the umbilical cord blood which was collected as stated above was centrifuged to separate mononuclear cells which were then seeded in culture dishes and cultured to a proper density after which the cells were passaged.

The composition of the present invention may further comprise an auxiliary component selected from the group consisting of a medium for suspending cells, a gene useful for the treatment of brain diseases (e.g., an anti-inflammatory cytokine gene), an inflammatory cytokine siRNA or antisense primer, an expression vector carrying the gene or the siRNA or antisense primer, an autocrine or paracrine cytokine (e.g. interleukin-10), a growth factor (e.g. keratinocyte growth factor), and a combination thereof. Herein, the medium may be the same as the culture medium, and don't contain serum, antibiotics, or antifungal agent.

The genes or the expression vector carrying the genes may be introduced into the cells using a well-known method, for example, viral transfection or non-viral transfection, or may simply be combined with the cells. For example, the gene delivery may be achieved by a technique including, but not limited to, adenoviral transfection, a gene gun, liposome-mediated transformation, retrovirus- or lentivirus-mediated transfection, plasmid transformation, and adeno-associated virus transfection. In addition, the cells may be applied together with a carrier containing a gene delivery medium designed for release or transfer of a gene into the cell over a long period of time.

The composition of the present invention may be used immediately or frozen until use. For cryopreservation, the cells may be mixed with a standard cryopreservative (e.g., DMSO, glycerol, or Epilife® cell freezing medium (Cascade Biologics)) before freezing.

In one embodiment of the present invention, the composition may be formulated into suitable single dosage forms using a method known in the pharmaceutical field.

In addition to the effective components stated above, the composition of the present invention may further comprise and at least one pharmaceutically acceptable carrier and may be formulated into various forms.

According to another aspect thereof, the present invention envisages the prophylaxis or therapy of cell proliferative diseases, such as cancer, by administering the composition into a subject in need thereof. As used herein, the term "subject" means an animal which needs the prevention or treatment of a disease of interest. The subject may include humans, non-human primates, and mammals such as mice, rats, dogs, cats, horses, cows, etc.

The effective dosage of the pharmaceutical composition in accordance with the present invention depends on various factors, including the patient's condition and weight, severity of diseases, kinds of drug formulation, route of administration, and the period of time of administration, and may be determined properly by those skilled in the art. In general, it may be administered in a single dose, or in multiple doses per day at a daily dose ranging from 0.001 to 100 mg/day, and preferably from 0.01 to 30 mg/kg.

An ampule for injection may be mixed and formulated with an injection solution just before use. In this regard, physiological saline, a glucose solution, a mannitol solution, or Ringer's solution may be used as the injection solution. The composition or pharmaceutical formulation according to the present invention may be administered together with a different kind of stem cells used for transplantation or other purposes, or in mixture with such stem cells using a typical method well-known in the art. Preferably, the composition or formulation may be directly grafted or transplanted into the cerebral ventricles or the airway of a subject in need thereof. In addition, the administration may be achieved using a non-surgical method, for example, using a catheter, or a surgical method, for example injection or transplantation, after thoracotomy. Preferred is non-surgical'administration. Typically, the composition or formulation may be parenterally administered, for example, directly into a lesion, or by intravascular infusion, such as in hematopoietic stem cell transplantation.

A better understanding of the present invention may be obtained through the following examples which are set forth to illustrate, but are not to be construed as limiting the present invention.

Example 1

Preparation of Intravascular Hemorrhage Model

To establish intravascular hemorrhage models, blood was taken in a total volume of 200 µL from the tail vein of a mother and injected at a dose of 100 µL/ventricle into the left and the right ventricle of 4 days-old rats anesthetized with nitrogen monoxide (NO) slowly over 5 min using a 31 gauge syringe. At one day post-injection, the brains of the 5-days old rats were scanned by 7-teslar MRI to examine intravascular hemorrhage.

The brain MRI images were subjected to volumetric analysis using the Image J program to calculate the ventricular dilatation according to total ventricular volume/total brain volume. All of the intraventricular hemorrhage-induced rats were found to exhibit significant ventricular dilatation due to the accumulation of a significant amount of blood in the ventricles, compared to normal rats (NC), as measured by MRI at 5 days post-birth.

Example 2

Administration of Umbilical Cord Blood-Derived Mesenchymal Stem Cells into Intraventricular Hemorrhage Model At 6 days post-birth, mesenchymal stem cells isolated from human umbilical cord blood were suspended in an amount of $1\times10^5$ cells in 10 µL of PBS and slowly injected into the right ventricle of the neonatal rats anesthetized with NO gas.

At 11 days post-birth, the brains of all the neonatal rats were scanned by 7-teslar MRI (T2, Flash) to monitor ventricular dilatation.

At 32 days post-birth, final brain MRI (T2, Flash) was performed to trace the change of ventricular dilatation.

Example 3

Preparation of Tissue Section

After the final MRI imaging, the neonatal rats were anesthetized by intraperitoneal injection of ketamine, and CSF was collected from the cisterna magna by cisternal tap with a 31 gauge syringe and frozen at −70° C. until use. The limbs were fixed before the rats were thoracotomized to expose the heart and the lungs. After a 23 gauge needle was fixed into the left ventricle, the right atrium was punctured and perfused with 4% paraformaldehyde. Then, an incision was made in the skull, and brain tissue was carefully taken and fixed in 4% formalin, or regions around the cerebral ventricles were sectioned, rapidly frozen in nitrogen gas, and stored at −70° C. until use.

Example 4

Distribution of Stem Cell Composition in Cerebral Ventricles

When a cellular therapeutic labeled with red fluorescent PHH26 and SPIO (super paramagnetic iron oxide), which is visualized as a low intensity signal in flash MRI, was transplanted to the cerebral ventricles, fluorescence microscopy showed that the cellular therapeutic was stably settled in the brain tissues of the intraventricular hemorrhage-induced rats (FIG. 1). In addition, after the cell transplantation, flash MRI images taken at 11 and 32 days post-birth showed that the distribution region of the low signal intensity around the cerebral ventricles and the brain tissues was incident with that of PKH26-positive cells.

Example 5

Comparison of Groups Administered with and without the Stem Cell Composition 5-1. Observation of Corpus Callosum Thickness Brain tissue fixed for 24 hours was embedded in paraffin, sectioned at a thickness of 5 µm, and stained with haematoxylin eosin, followed by optical microscopy to examine the thickness of the corpus callosum at a bregma level.

Figure 2:
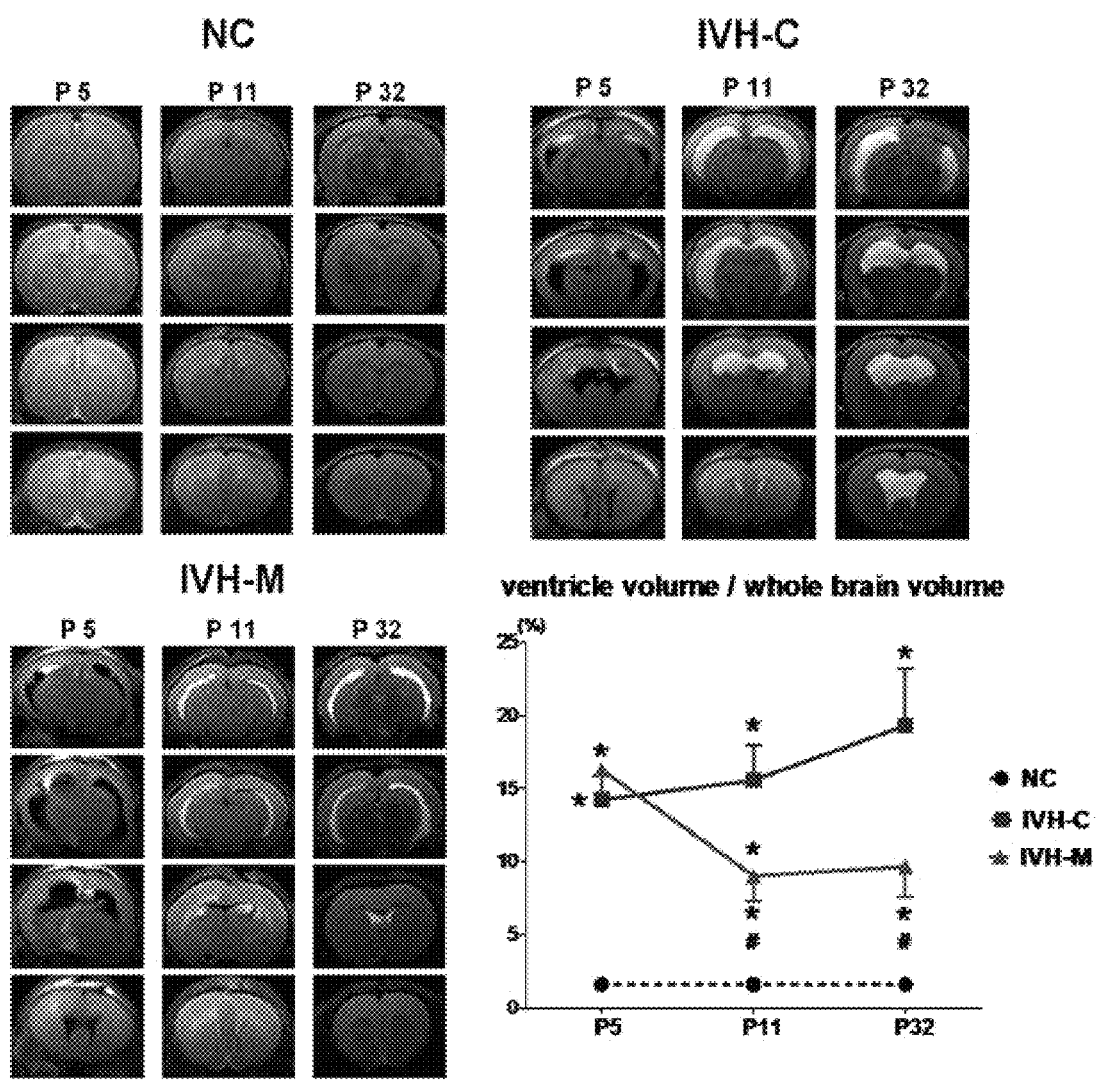
FIG. 2 shows that ventricular dilatation induced by intraventricular hemorrhage is reduced in rats intraventricularly injected with stem cells (IVH-M), compared to non-treated rats (IVH-C)

After the induction of intravascular hemorrhage, the rats intraventricularly injected with the stem cells (IVH-M) were found to have reduced ventricular dilatation with statistic significance, compared to non-treated rats (IVH-C), as measured by the brain MRI at 11 days post-birth (FIG. 2).

The finding that the stem cell-injected group had reduced ventricular dilatation was true of the brain MRI taken at 32 days post-birth. After coronal sections of the brain were stained with haematoxylin and eosin, the corpus callosum was remarkably thinned in the intraventricular hemorrhage model, compared to the normal rats (NC). However, the group intraventricularly injected with the cellular therapeutic (IVH-M) had significantly thicker corpora callosa than did the non-treated group (IVH-C).

Figure 3:
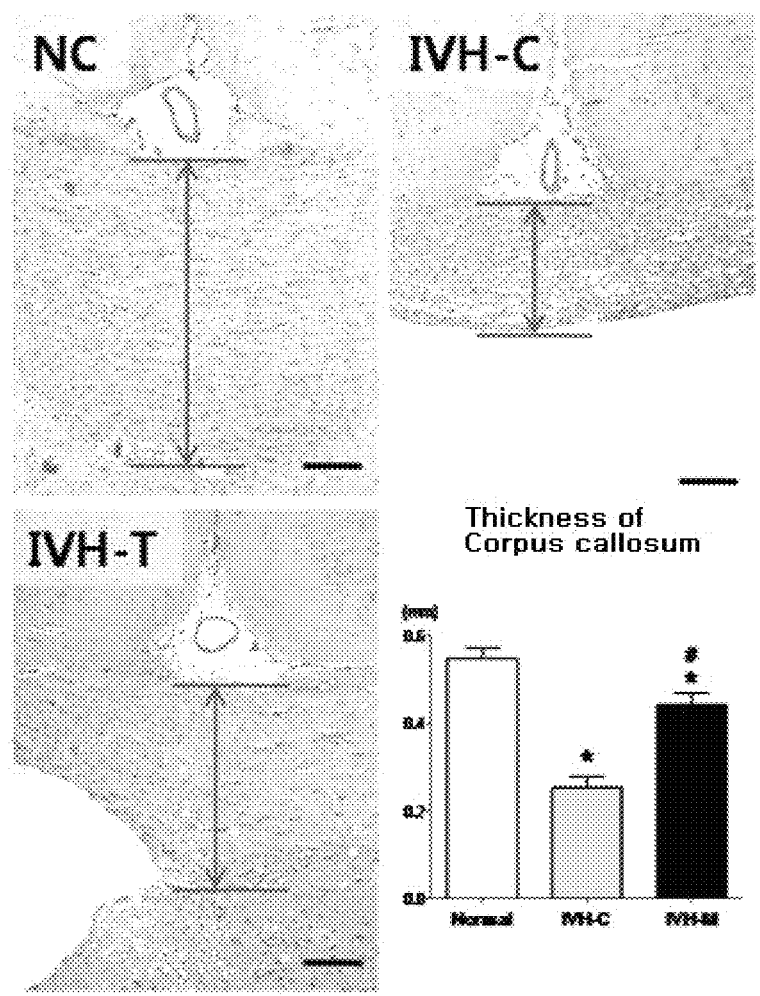
FIG. 3 shows that the intraventricular injection of stem cells increases the thickness of the corpus callosum, the cerebral parenchyma adjacent to the cerebral ventricles.

These results indicate that the ventricular dilatation which was aggravated after the induction of intraventricular hemorrhage can be improved by intraventricular injection of stem cells, leading to an increase in the thickness of the corpus callosum, the brain parenchyma adjacent to the cerebral ventricles (FIG. 3).

5-2. Measurement of Apoptosis, Gliosis of the Brain and Myelination of the Brain Deparaffinized tissue sections were used to quantitatively analyze apoptosis, gliosis, and myelination on the brain by an immunofluorescence method using immunofluorescent terminal deoxynycleotidyltransferase-mediated deoxyuridine triphosphate nick end labeling (TUNEL), neuronal specific glial fibrillary acidic protein (GFAP), and myelin basic protein (MBP), respectively. Three sections were randomly taken from a region ranging from +0.95 mm anterior to the bregma to −0.11 mm posterior to the bregma Three randomly selected parts in each section were examined under a microscope, and a statistical analysis was preformed with mean values of the three measurements.

1) Reduction of Apoptotic Cells by Injection of the Stem Cell Composition (TUNEL Staining)

When staining coronal sections of brain tissue was observed using immunofluorescence staining, the count of the TUNEL-positive cells in tissue around the ventricles, that is, the count of apoptotic cells, was greatly increased in the intraventricular hemorrhage-induced rats, compared to the normal rats (NC). The IVH-M group, which was treated with stem cells, had a significantly lower count of apoptotic cells, compared to the IVH-C group, not treated with stem cells (FIG. 4).

2) Reduction of Gliosis by Injection of the Stem Cell Composition (GFAP Staining)

Figure 4:
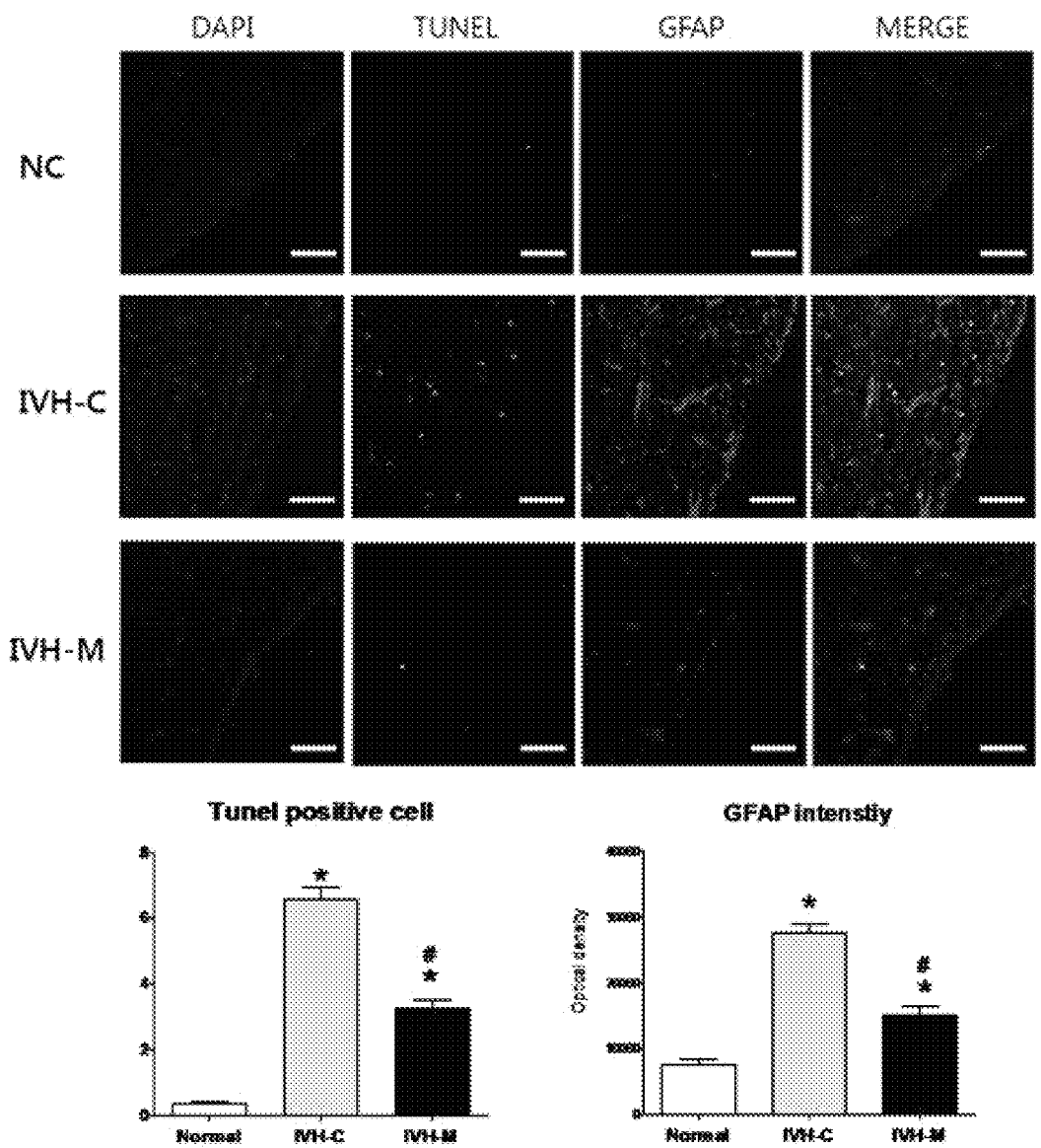
FIG. 4 shows counts of apoptotic cells and intensity of gliosis in IVH-M and IVH-C, which were treated with and without stem cells, respectively.

A GFAP assay for gliosis of the brain showed a result similar to that of the apoptosis assay (FIG. 4).

3) Increase of Myelination by Injection of the Stem Cell Composition (MBP Staining)

Figure 5:
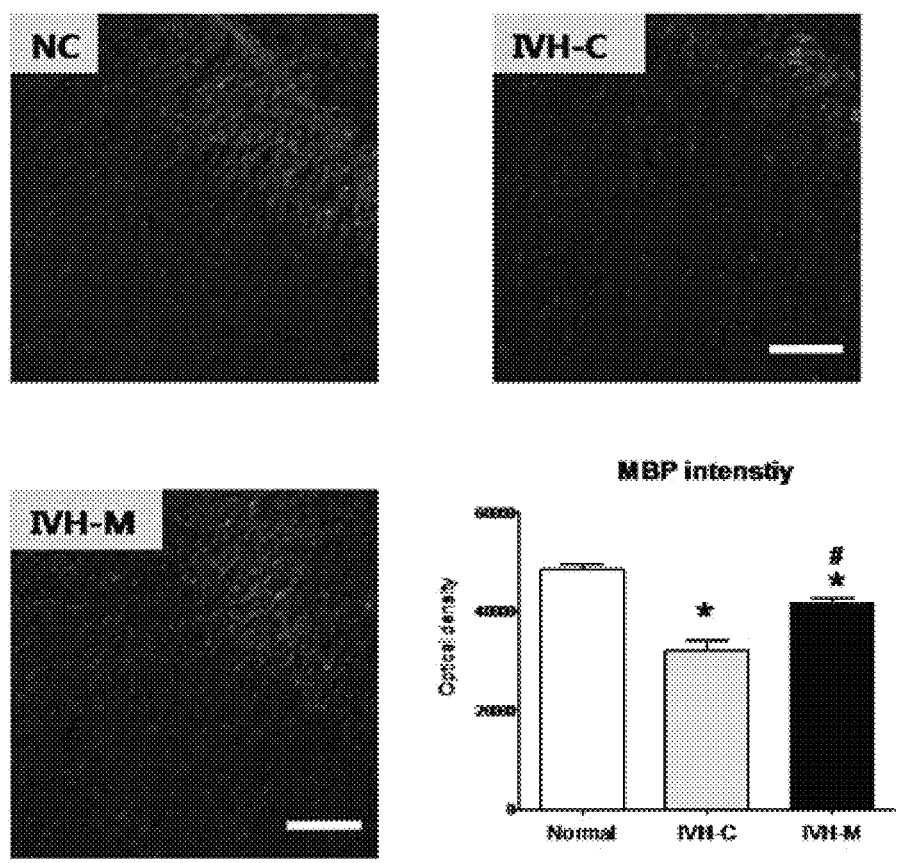
FIG. 5 shows that the injection of stem cells increases neural myelination.

The intraventricular hemorrhage model rats were remarkably lower in MBP intensity, indicative of the degree of myelination, than was the normal control (NC). A significant increase in MBP intensity was observed in the IVH-M group, which was treated with stem cells, compared to the IVH-C group, not treated with stem cells. That is, the injection of stem cells significantly improved the myelination (FIG. 5).

5-3. Reduction of the Level of Inflammatory Cytokine in Cerebrospinal Fluid by Injection of the Stem Cell Composition The cryopreserved ventricular tissue and cerebrospinal fluid were examined for the level of inflammatory cytokines (IL-1α, IL-1β, IL-6, TNF-α) using enzyme-linked immunosorbent assay (ELISA).

Figure 6:
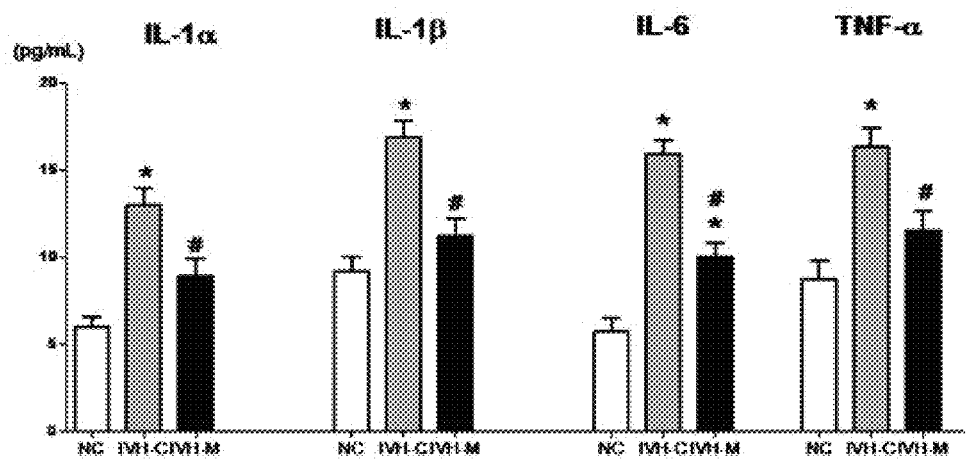
FIG. 6 shows levels of inflammatory cytokines in IVH-M and IVH-C groups.
Figure 6:
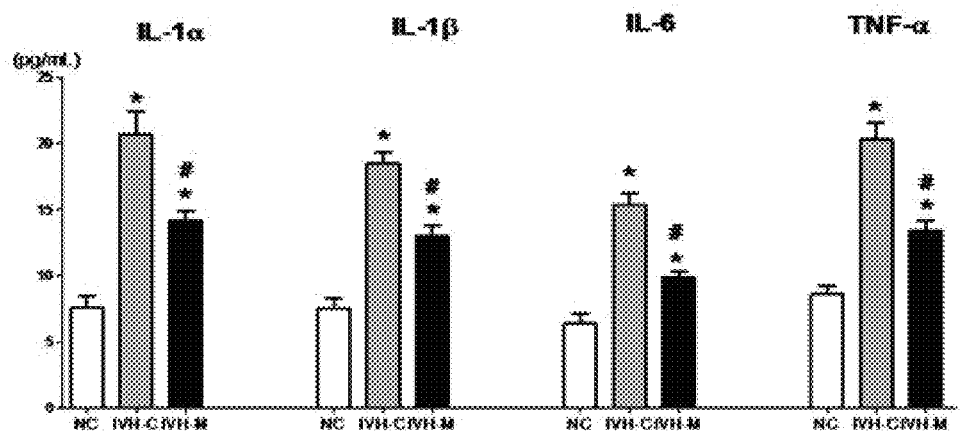

Higher levels of inflammatory cytokines in ventricular tissue and cerebrospinal fluid were found from the intraventricular hemorrhage model rats than the normal control (NC). The IVH-M group was observed to have a significantly decreased level of the intraventricular hemorrhage-induced inflammatory cytokines, compared to the IVH-C group (FIG. 6). These results indicate that inflammation around the cerebral ventricles, induced by intraventricular hemorrhage, can be improved by treatment with stem cells.

Example 6

Comparison of Therapeutic Effect between Umbilical Cord Blood-Derived Mesenchymal Stem Cells and Umbilical Cord Blood-Derived Mononuclear Cells Taking prior art literature concerning the therapeutic effects of umbilical cord blood-derived cells on intraventricular hemorrhage into consideration, the following experiment was carried out to compare effects between the mesenchymal stem cells and the mononuclear cells, predominant over other cells in umbilical cord blood.

Rat L2 cells were incubated for 60 min with $H_2O_2$ and co-cultured with umbilical cord blood-derived mesenchymal stem cells or mononuclear cells.

Thereafter, an examination was made of the survival of the rat L2 cells and the level of the cytokines secreted from the rat L2 cells. The L2 cells co-cultured with the umbilical cord blood-derived mesenchymal stem cells (HUM group) outlived those co-cultured with the umbilical cord blood-derived mononuclear cells (HMN group). In addition, not only the growth factors with restorative function, VEGF and HGF, but also LIF (leukemia inhibitory factor), which is very important for an inflammation-suppressive, immuno-modulating effect, were detected at higher levels in the HUM group than the HMN group.

Figure 7:
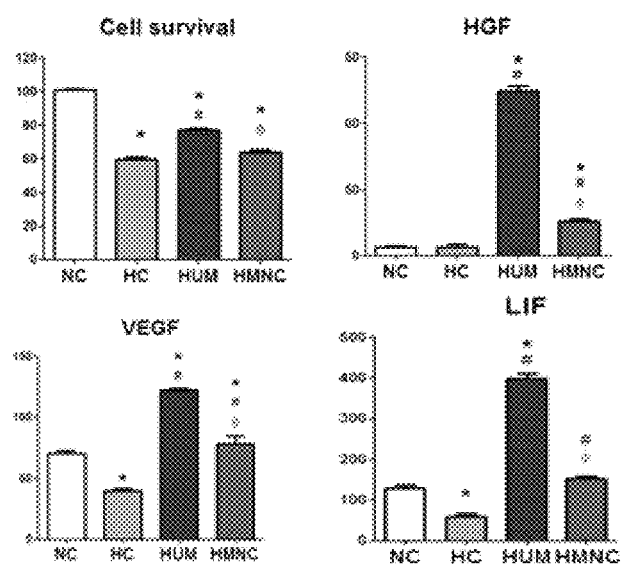
FIG. 7 shows therapeutic effects of umbilical cord blood-derived mesenchymal stem cells and umbilical cord blood-derived mononuclear cells.

Taken together, the data obtained above demonstrates that mesenchymal stem cells increase the survival of oxidative stress-damaged cells and release higher levels of anti-inflammatory cytokines and growth factors, compared to umbilical cord blood-derived mononuclear cells (FIG. 7).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of treating intraventricular hemorrhage in a preterm infant, comprising:
    transplantinq allogeneic mesenchymal stem cells into a subject in need of treatment,
    and
    wherein the transplantation of mesenchymal stem cells is performed by intraventricular route or intravascular route.

2. The method of claim 1, wherein the mesenchymal stem cells are selected from the group consisting of umbilical cord blood-, adipose tissue-, skin-, or bone marrow-derived mesenchymal stem cells, mesenchymal stem cells proliferated from the umbilical cord blood-, adipose tissue-, skin-, or bone marrow-derived mesenchymal stem cells by passage, and combinations thereof.

3. The method of claim 1, wherein the transplantation of mesenchymal stem cells is by allograft.

4. The method of claim 1, comprising further administering an auxiliary component selected from the group consisting of a culture medium, an anti-inflammatory cytokine gene, siRNA or anti-sense primer against inflammatory cytokine, an expression vector carrying the siRNA or anti-sense primer, interleukin-10, a growth factor, and a combination thereof.

5. The method of claim 1, wherein the transplantation of mesenchymal stem cells attenuates ventriculomegaly.

6. The method of claim 1, wherein the transplantation of mesenchymal stem cells attenuates cell death.

7. The method of claim 1, wherein the transplantation of mesenchymal stem cells improves impaired neural myelination.

8. The method of claim 1, wherein the transplantation of mesenchymal stem cells reduces the level of inflammatory cytokines.

* * * * *